US011878031B2

(12) United States Patent
Calomme et al.

(10) Patent No.: US 11,878,031 B2
(45) Date of Patent: Jan. 23, 2024

(54) SILICIC ACIDS FOR USE IN THE TREATMENT OF PERIODONTITIS (71) Applicant: Bio Minerals N.V., Destelbergen (BE)

(72) Inventors: Mario Remi Yvonne Calomme, Edegem (BE); Kathleen Jozef Ingrid Suzanne Van Hoof, Lanaken (BE)

(73) Assignee: Bio Minerals N.V., Destelbergen (BE)

( * ) Notice: Subject to any disclaimer, the term of this patent is extended or adjusted under 35 U.S.C. 154(b) by 330 days.

(21) Appl. No.: 17/281,811

(22) PCT Filed: Oct. 4, 2019

(86) PCT No.: PCT/EP2019/076944
§ 371 (c)(1),
(2) Date: Mar. 31, 2021

(87) PCT Pub. No.: WO2020/070300
PCT Pub. Date: Apr. 9, 2020

(65) Prior Publication Data
US 2022/0008454 A1 Jan. 13, 2022

(30) Foreign Application Priority Data
Oct. 5, 2018 (EP) .................................... 18198972

(51) Int. Cl.
*A61K 33/00* (2006.01)
*A61P 1/02* (2006.01)
*A61K 9/00* (2006.01)
*A61K 31/122* (2006.01)
*A61K 31/375* (2006.01)
*A61K 31/593* (2006.01)
*A61K 33/04* (2006.01)
*A61K 33/06* (2006.01)
*A61K 33/22* (2006.01)
*A61K 33/30* (2006.01)
*A61K 33/34* (2006.01)
*A61K 35/741* (2015.01)
*A61K 45/06* (2006.01)

(52) U.S. Cl.
CPC ............ *A61K 33/00* (2013.01); *A61K 9/0053* (2013.01); *A61K 31/122* (2013.01); *A61K 31/375* (2013.01); *A61K 31/593* (2013.01); *A61K 33/04* (2013.01); *A61K 33/06* (2013.01); *A61K 33/22* (2013.01); *A61K 33/30* (2013.01); *A61K 33/34* (2013.01); *A61K 35/741* (2013.01); *A61K 45/06* (2013.01); *A61P 1/02* (2018.01)

(58) Field of Classification Search
CPC .... A61K 33/00; A61K 9/0053; A61K 31/122; A61K 31/375; A61K 31/593; A61K 33/04; A61K 33/06; A61K 33/22; A61K 33/30; A61K 33/34; A61K 35/741; A61K 45/06; A61P 1/02
See application file for complete search history.

(56) References Cited

U.S. PATENT DOCUMENTS

| 4,985,405 | A | 1/1991 | Gueyne et al. | |
| 8,771,757 | B2 | 7/2014 | Berghe | |
| 8,852,631 | B2 | 10/2014 | Cade et al. | |
| 9,655,860 | B2 | 5/2017 | Cade et al. | |
| 2010/0303737 | A1* | 12/2010 | Hurtig ...................... | A61K 8/98 424/48 |
| 2016/0324766 | A1* | 11/2016 | Stettler et al. ......... | A61K 38/05 |
| 2021/0023125 | A1 | 1/2021 | Calomme et al. | |

FOREIGN PATENT DOCUMENTS

| BE | WO 2004/016551 A1 * | 2/2004 | ............... A61K 9/16 |
| EP | 0743922 A1 | 11/1996 | |
| EP | 1391426 A1 | 2/2004 | |
| EP | 1551763 B1 | 4/2009 | |
| EP | 3117822 A1 | 1/2017 | |
| EP | 3396065 A1 | 10/2018 | |
| EP | 3549578 A1 | 10/2019 | |
| JP | 2005239653 A | 9/2005 | |

(Continued)

OTHER PUBLICATIONS

Tim D Spector et al. Choline-stabilized orthosilicic acid supplementation as an adjunct to CalciumNitamin D3 stimulates markers of bone formation—BMC Musculoskeletol Disorders 2008, 9:85 doi: IO. I I 86/ 1471-2474-9-85 (Year: 2008).*

Piet Geusens, A 12-week randomized, double-blind, placebo-controlled multicenter study of choline-stabilized orthosilicic acid in patients with symptomatic knee osteoarthritis Geusens et al. BMC Musculoskeletal Disorders (2017) 18:2 DOI 10.1186/s12891-016-1370-7 (Year: 2017).*

TimDSpectoretal.Choline—stabilizedorthosilicicacidsupplementationasanadjuncttoCalciumNitaminD3stimulatesmarkersofbone formation—BMC MusculoskeletolDisorders2008,9:85doi:IO.86/1471-2474-9-85 (Year: 2008).*

(Continued)

*Primary Examiner* — Robert A Wax
*Assistant Examiner* — Andre Mach
(74) *Attorney, Agent, or Firm* — McDonnell Boehnen Hulbert & Berghoff LLP (57) ABSTRACT

The oral administration of bioavailable silicic acid, such as choline-stabilized silicic acid during a period of at least 3 months daily leads to the prevention, inhibition and or treatment of periodontitis and peri-implantatis. The treatment is particularly suitable in combination with appropriate cleaning of the teeth and disinfecting the mouth, by one or more antiseptic and/or antimicrobial agent(s), as carried out at least once and suitably regularly, such as once per year, twice per year, four times per year or even every second month or every month. The treatment may be further enhanced by simultaneous administration of vitamins, trace elements, as well as by administration of a probioticum. Such additional agents may be applied separately, but are preferably incorporated in the formulation of bioavailable silicic acid.

19 Claims, 5 Drawing Sheets

(56) References Cited

FOREIGN PATENT DOCUMENTS

| JP | 2006117601 A | 5/2006 |
|---|---|---|
| WO | 95/21124 A1 | 8/1995 |
| WO | 9521124 A1 | 8/1995 |
| WO | 2006082842 A1 | 8/2006 |
| WO | 2009018356 A1 | 2/2009 |
| WO | 2009127256 A1 | 10/2009 |
| WO | 2010092925 A1 | 8/2010 |
| WO | 2012032364 A1 | 3/2012 |
| WO | 2012035364 A1 | 3/2012 |
| WO | 2013/133781 A1 | 9/2013 |
| WO | 2014006532 A1 | 1/2014 |
| WO | 2019/193200 A1 | 10/2019 |
| WO | 2019193200 A1 | 10/2019 |
| WO | 2020070300 A1 | 4/2020 |
| WO | 2020/094886 A1 | 5/2020 |

OTHER PUBLICATIONS

Piet Geusens, A 12—week randomized, double-blind, placebo-controlled multicenter study of choline-stabilized orthosilicic acid in patients with symptomatic knee osteoarthritis Geusen set al. BMC Musculoskeletal Disorders (2017) 18:2 DO! 10.1186/s12891-016-1370-7 (Year: 2017).*
"Advanced Collagen Generator Supplement", Feb. 5, 2015. [Retrieved from www.gnpd.com, Database Accession No. 2931269].
"Food Supplement", Mar. 3, 2010. [Retrieved from www.gnpd.com, Database Accession No. 1279883].
"E & Selenium Food Complex", Oct. 12, 2009. [Retrieved from www.gnpd.com, Database Accession No. 1192260].
"Bone Collagenizer Ultra Capsules", Oct. 30, 2017. [Retrieved from www.gnpd.com, Database Accession No. 5196303].
"Multi Vitamin Bar", Mar. 16, 2015. [Retrieved from www.gnpd.com, Database Accession No. 3034249].
PCT International Search Report and Written Opinion, PCT International Application No. PCT/EP2019/058802, dated Jun. 24, 2019.
Barel, A. et al., "Effect of oral intake of choline-stabilized orthosilicic acid on skin, nails and hair in women with photodamaged skin," Archives of Dermatological Research, vol. 297, No. 4, pp. 147-153, Oct. 1, 2005.
Examination Report issued in Indian Patent Application No. 202027048003 dated Jul. 7, 2022.
Examination Report issued in European Patent Application No. 18166152.1 dated May 31, 2022.
M. Biyani, "Choosing Capsules: A Primer," Pharmaceutical Technology 41 (10) 2017.
BioSil Liquid Capsules ([online] retrieved on Aug. 8, 2022 from https://www.amazon.com/Capsules-Natural-Factors_Collagen_Generator/dp/B07ZMHLKP9; 2019;9 pages) (Year: 2019).
Spector, T.D., et al., "Choline-Stabilized Orthosilicic Acid Supplementation as an Adjunct to Calcium/Vitamin D3 Stimulates Markers of Bone Formation in Osteopenic Females: A Randomized, Placebo-Controlled Trial", BMC Musculoskeletal Disorders, Jun. 11, 2008, vol. 9(1).
Teughels, W., et al., "Clinical and Microbiological Effects of Lactobacillus Reuteri Probiotics in the Treatment of Chronic Periodontitis: A Randomized Placebo-Controlled Study", Journal of Clinical Periodontology, Sep. 15, 2013, vol. 40(11), pp. 1025-1035.
International Search Report from the European Patent Office, dated Dec. 17, 2019, for International Application No. PCT/EP2019/076944, pp. 1-5.
Written Opinion of the International Searching Authority, dated Dec. 17, 2019, for International Application No. PCT/EP2019/076944, pp. 1-11.
Calomme, M.R., et al., "Supplementation of Calves with Stabilized Orthosilicic Acid. Effect on the Si, Ca, Mg, and P Concentrations in Serum and the Collagen Concentration in Skin and Cartilage", Biol. Trace Elem. Res., Feb. 1997, vol. 56(2), pp. 153-165.
Calomme, M., et al., "Partial Prevention of Long-Term Femoral Bone Loss in Aged Ovariectomized Rats Supplemented with Choline-Stabilized Orthosilicic Acid", Calcif Tissue Int., Apr. 2006, vol. 78(4), pp. 227-232, Epub Apr. 13, 2006.
Chiwele, I., et al., The Shell Dissolution of Various Empty Hard Capsules, Chem. Pharm. Bull., Jul. 2000, vol. 48(7), pp. 951-956.
Geusens, P., et al., "A 12-Week Randomized, Double-Blind, Placebo-Controlled Multicenter Study of Choline-Stabilized Orthosilicic Acid in Patients with Symptomatic Knee Osteoarthritis", BMC Musculoskeletal Disorders, Jan. 2017, vol. 18(2), pp. 1-12.
Iler, R.K., "The Chemistry of Silica", John Wiley & Sons, NY, 1979, pp. 1-2, 10-15 and 172-189.
Jugdaohsingh, R., et al., "Oligomeric but not Monomeric Silica Prevents Aluminum Absorption in Humans", Am. J. Clin. Nutr., Apr. 2000, vol. 71(4), pp. 944-949.
Rabadiya, et al., "A Review: Capsule Shell Material from Gelatin to Non-Animal Origin Material", International Journal of Pharmaceutical Research and Bio-Science, 2013, vol. 2(3), pp. 42-71.
Wickett, R.R., et al., "Effect of Oral Intake of Choline-Stabilized Orthosilicic Acid on Hair Tensile Strength and Morphology in Women with Fine Hair", Arch. Dermatol. Res., Oct. 2007, vol. 299, pp. 499-505.
"Choline-Stabilised Orthosilicic Acid Added for Nutritional Purposes to Food Supplements", The EFSA Journal, 2009, vol. 948, pp. 1-23.
Jivan, et al., "Preparation of cold water-soluble potato starch and its characterization." Journal of food science and technology 51, No. 3 (2014): 601-605.
M. Biyani, "Choosing Capsules: A Primer," Pharmaceutical Technology 41(10) 2017 pp. 36-41.
BioSil Liquid Capsules ([online] retrieved on Apr. 13, 2022 from: https://www.amazon.com/Capsules-Natural-Factors-Collagen-Generator/dp/B07ZMHLKP9; 2019:12 pages) (Year: 2019).
Lorna Vanderhaeghe [online] retrieved on Jun. 30, 2023 from: https://www.naturallyhealthyniagara.com/pdf/ProductInformationSheet-BioSil.pdf; dated Sep. 27, 2017; 3 pages.
BioSil ch-OSA Advanced Collagen Generator, 30 Vegetarian Capsules [online] retrieved on Jun. 30, 2023 from: https://www.iherb.com/pr/ biosil-ch-osa-advanced-collagen-generator-30-vegetarian-capsules/23156; dated Mar. 2010; 8 pages.

* cited by examiner

Before ch-OSA®  After ch-OSA®
Fig. 4A  Fig. 4B

Baseline    6 months ch-OSA®    1 year ch-OSA®
Fig. 5A     Fig. 5B              Fig. 5C

Fig. 6

SILICIC ACIDS FOR USE IN THE TREATMENT OF PERIODONTITIS

CROSS-REFERENCE

This application is a 371 U.S. national phase of PCT/EP2019/076944, filed Oct. 4, 2019, which claims priority from European patent application no. 18198972.4, filed Oct. 5, 2018, both which are incorporated by reference in its entirety.

FIELD OF THE INVENTION

The invention relates to a compound and a pharmaceutical composition for use in the prevention, inhibition and/or treatment of periodontitis and/or peri-implantitis.

BACKGROUND OF THE INVENTION

Periodontitis and peri-implantitis are dental diseases. Periodontal destruction in periodontitis is triggered by the host's response to pathogenic bacteria that have been allowed to accumulate on the teeth, initially causing inflammation of the gums and eventually leading to destruction of the periodontal ligament and the supporting bone. The latter can result in loosening and potential loss of teeth. In peri-implantitis, hard tissues around a dental implant are degenerated resulting in bone loss and potential loss of the implant. Both diseases are initiated with periodontal pathogens and both have similar clinical presentations, including deep probing depths and bleeding. Even the microbiology cultivated from both are similar. Histologically and pathologically the diseases vary. Most importantly to clinicians, the diseases do not respond to treatment similarly. Currently, there is no appropriate non-invasive treatment for any of these diseases. For sake of good understanding, the two diseases will now be discussed in more detail.

Periodontitis

Periodontitis is an infectious disease resulting in an often painless destruction of the tooth supporting tissue, the periodontium. In fact the normal periodontium provides the necessary support to maintain teeth in function. It consists of four principal components: the gingiva, the periodontal ligament, the cementum and alveolar bone. In all these four components, collagenous fibers have an important structural role as it determines the biomechanical properties of the tissue. Periodontitis involves progressive loss of the alveolar bone around the teeth, and if left untreated, can lead to the loosening and subsequent loss of teeth. Periodontitis furthermore enhances the risk for various systemic diseases including atherosclerosis, coronary heart disease, stroke and infants with low birth weight. This destruction of the periodontium is caused by a mixture of microorganisms (called plaque) in the periodontal pocket, which is the habitat between the tooth roots and gingival), in a direct way and/or an indirect way. The direct way involves the effect of enzymes from pathogenic species. The indirect way involves an inflammatory host response to bacterial antigens.

Seven major categories of periodontal diseases are distinguished of which 2-6 are termed destructive periodontal disease, because the damage is essentially irreversible. The seven categories are 1. Gingivitis; 2. Chronic periodontitis; 3. Aggressive periodontitis; 4. Periodontitis as a manifestation of systemic disease; 5. Necrotizing ulcerative gingivitis/periodontitis; 6. Abscesses of the periodontium; 7. Combined periodontic-endodontic lesions. If up to 30% of sites in the mouth are affected, the manifestation is classified as "localized"; for more than 30%, the term "generalized" is used.

The "severity" of the disease relates to the amount of periodontal, collagenous ligament fibers that have been lost, resulting in "clinical attachment loss" and the presence of 'pockets'. According to the American Academy of Periodontology, severity is subdivided into mild, moderate and severe, wherein mild means 1-2 mm of attachment loss; moderate means 3-4 mm of attachment loss and severe means ≥5 mm (0.20 in) of attachment loss.

The development of periodontitis starts with an inflammation triggered by dental plague. As dental plaque or biofilm accumulates on the teeth near and below the gums, there is a shift in the composition of the biofilm from essentially *Streptococcus* to an *Actinomyces* dominant plaque. Motile bacteria is also seen more frequently. As this happens, inflammation sets in the gingiva. Initially, this takes the form of gingivitis, which represents inflammation confined to the soft tissues above the bone level. Inflammation in the gingiva can remain at the gingivitis level for a long period and will not progress to periodontitis, unless in the presence of local conditions or generalized host susceptibility. In this case, the immune system's response to plaque accumulation shifts from a predominantly neutrophilic mediated response to lymphocytic and plasma cell-mediated response. Clinically, the gingiva presents swelling, redness and a tendency to bleed. This modifies the environment, leading to changes in the composition of the biofilm itself. As this happens, a predominantly gram-negative environment is established, with periodontal pathogens emerging. These include *A. actinomycetemcomitans*, the red complex bacteria (*P. gingivalis, T. forsythia, T. denticola*) and to a lesser extent the orange complex bacteria (*F. nucleatum, P. micros, P. intermedia, P. nigrecens, E. nodatum* and *S. constellates*). Strongest bacterial association to chronic periodontitis is with *P. gingivalis*. Numerous virulence factors have been identified for this pathogen. This allows *P. gingivalis* to elude defense mechanism and perpetuate inflammation inside the periodontium. Prolonged inflammation in the periodontium leads to an apical shift in the attachment of the gingiva to the tooth with deepening pockets and bone loss around the teeth. Untreated periodontitis progresses unevenly over time but results in loss of function, tissue destruction, and tooth loss.

Primary treatment of periodontitis is focused on removing the bacterial plaque and the resulting hardened calculus ("tartar"). Good hygiene instructions such as frequent brushing and flossing help prevent plaque accumulation but professional cleaning by a dentist is necessary to remove the hardened plaques, i.e. "scaling" means scraping off the tartar from above and below the gumline and "root planing" involves special instruments to remove tough calculus and bacteria deposits along the root surfaces under local anaesthesia. Despite these treatments patients may keep residual, deep pockets. At present non-invasive treatments are not available to treat the loss of connective tissue which is causing residual, deep pockets. Only invasive, gum surgery is applied to reduce the pocket depth, often in combination with bone or tissue grafts or special materials to replace or stimulate new growth of bone or gum tissue.

Teughels et al., *J. of Clinical Periodontology*, 40(2013), 1025-1035, discloses the admission of a composition of certain "beneficial" bacteria in order to improve the bacterial flora in the mouth of chronic periodontitis patients. The beneficial bacteria strain is *Lactobacillus reuteri*. According to the authors, the clinical results showed a clinically relevant benefit for the patient as "risk for disease progression" and "need for additional surgery" outcome measures were significantly better when *L. reuteri* lozenges were used as an adjunct to scaling and root planning (SRP) and oral hygiene instructions. The authors further observe that although initially the number of pathogens in the bacterial flora can be greatly reduced by SRP, periodontal-pathogens quickly re-colonize the treated niches in the oral cavity.

Peri-Implantitis

For many years, dental implants prove to be a good replacement when one or more teeth are missing. Although there is a high clinical success rate in terms of the survival rate of implants, problems with inflammation around already osseo-integrated implants are frequently reported. When this inflammatory process is limited to the soft tissues around the implant, one speaks of peri-implant mucositis. Peri-implantitis, on the other hand involves degeneration of the hard tissues surrounding the implant, with bone loss and pocket formation as a result. It is not observed upon the placement of an implant, but only found several years afterwards. Five to ten years after implant placement one out of five patients suffers from peri-implantitis.

Peri-implantitis is not only frequent, but a serious complication. Implants are expensive but have the potential to last a patient's entire life. Unfortunately, peri-implantitis can lead to disintegration and early loss of implants and their supported prostheses.

To treat peri-implantitis, one may approach it similarly to periodontitis as both diseases share many features. Both diseases can be initiated with periodontal pathogens and both have similar clinical presentations, including deep probing depths and bleeding. Even the microbiology cultivated from both are similar. But histologically and pathologically the diseases vary. The microbiology of peri-implantitis is more diverse than that of periodontitis. Histologically, peri-implantitis is much more infiltrative near the alveolar crest and often lacks a protective layer of tissue over the bone as we typically see in periodontitis. But most importantly to clinicians, the diseases do not respond to treatment similarly.

Peri-implantitis lesions do not respond well to improved oral hygiene and professional cleanings as with periodontitis. This is not to understate the importance of oral hygiene and professional maintenance in the prevention of peri-implantitis. But once peri-implantitis develops, conservative therapy appears ineffective. Non-surgical treatment of peri-implantitis using laser or air abrasive systems has shown poor results. Studies evaluating chemotherapeutics and mechanical debridement show minimal resolution. A recent study attempting the use of photodynamic therapy to treat peri-implantitis lesions was also unsuccessful. In summary, non-surgical treatments have not been able to predictably arrest peri-implantitis.

Therefore, there is a need for an improved non-invasive, non-surgical therapy, since professional cleaning (disinfection of the oral cavity) and the use of specific probiotic bacteria has not shown to be curative, i.e. it takes away the cause of the infection, at least partially, but regeneration of the gingiva and the alveolar bone is not accomplished by these treatments. Furthermore, the authors observe that the results are merely valid for the specific bacteria. Clearly, the colonization of such bacteria may heavily depend on both food of an individual and development of the oral cavity.

SUMMARY OF THE INVENTION

It is therefore an object of the present invention to provide improved, non-invasive, non-surgical prevention, inhibition and/or treatment for periodontitis and for peri-implantitis, which are not dependent on success of colonization of certain bacteria.

It is a further object to provide a compound and a pharmaceutical composition for use in the prevention, inhibition and/or treatment of periodontitis and peri-implantitis.

According to a first aspect, the invention provides a bioavailable silicon compound for oral use in prevention, inhibition and/or treatment of periodontitis and/or peri-implantitis.

According to a second aspect, the invention provides a pharmaceutical composition for oral administration comprising a bioavailable silicon compound for use in prevention, inhibition and/or treatment of periodontitis and/or peri-implantitis.

According to a third aspect, the invention provides a method of treatment of periodontitis and/or peri-implantitis comprising the oral administration of a bioavailable silicon compound.

The bioavailable silicon compound is particularly of the formula $Y_xSi(OH)_{4-x}$, wherein Y is optionally substituted $(C_1-C_4)$alkyl, $(C_2-C_5)$-alkenyl, $(C_1-C_4)$-alkoxy, amino and x is 0-2, and/or oligomers thereof. More preferably x=0.

It has been surprisingly and unexpectedly found that the oral administration of a bioavailable silicon compound can reduce clinical symptoms of periodontitis and peri-implantitis.

More particularly, probe pocket depth (PPD) and bleeding on probing (BOP) improved in periodontitis and bone regrowth was observed in peri-implantitis when orally administrating a silicon compound in the form of tablet, granules, capsule or a liquid. The administration of a bioavailable silicon compound has turned out effective in the inhibition and the treatment of ongoing and also chronic periodontitis. The administration of a bioavailable silicon compound has further turned out effective in the treatment of peri-implantitis. Although the probe pocket depth was not measured in the experiments, so as not to risk loss of implant, remarkable improvements in bone regrowth have been observed and documented by means of X-ray photos.

The oral administration of the silicon compound has been found successful for the reduction of the probe pocket depths and bleeding on probing in periodontitis patients having deep pockets of more than 4 mm depth on one or more teeth even in the case of residual, deep pockets. Residual pockets means pockets which remain present even after scaling and root planing. In the case of a residual, deep pocket there is considerable risk over time that a tooth or an implant may become completely detached and lost. It is deemed surprising that the administration of a silicon compound is effective at such advanced state of periodontitis and peri-implantitis, as current practitioners (such as dentists) consider such advanced states as rather untreatable.

In view of the surprising results obtained at in particular advanced states of the diseases, the oral administration of bioavailable silicon compound is also beneficial for patients that are at a risk of developing periodontitis and/or peri-implantitis, and/or for patients at which the said diseases are at an early stage. Particularly, when the oral administration of bioavailable silicon compound would be prescribed for any patient receiving an implant during a treatment period, for instance at least 6 months or preferably at least 12 months, it is deemed that the overall risk to develop peri-implantitis will be reduced. The administration of bioavailable silicon compound in the form of silicic acid with a choline stabilizer is deemed even more favourable, as choline is deemed beneficial for collagen, which is necessary so that the implant is well encapsulated by the tissue.

In one preferred embodiment, the silicon compound is used in a treatment for patients with severe, generalized periodontitis with an attachment loss of at least 5 mm prior to initial non-surgical periodontal therapy, and even more preferably of at least 6 mm attachment loss. The term 'generalized periodontitis' is used for a situation wherein a majority of the teeth is affected, such as at least 8 teeth, especially at least 10 teeth, or even at least 14 affected teeth, when 14 teeth are present. If the number of teeth is less than 14, 8-14 teeth should be affected. The treatment is particularly useful for patients having a minimum of 3 natural teeth in every quadrant. The use of the bioavailable silicon compound is herein preferably combined with the local application of an antiseptic agent. Furthermore, particularly in relation to such generalized periodontitis, it is deemed beneficial to apply at least one of an antibiotics and a probiotic strain locally.

The oral administration of a bioavailable silicon compound is also specifically advantageous for patients with aggressive periodontitis. The term 'aggressive periodontitis' refers the appearance of periodontist in people who, in most cases, otherwise appear healthy and do not have a high level of plague. It tends to have a familial aggregation and there is a rapid rate of disease progression. Aggressive periodontitis occurs in localized and generalized forms. Aggressive periodontitis may be due to the presence of bacteria. Therefore, the treatment preferably involves the oral administration of a bioavailable silicon compound in combination with the administration of antibiotics.

In an alternative embodiment, the silicon compound is used in a treatment for patients with peri-implantitis. For treatment of peri-implantitis, administration during at least one year is highly preferred to achieve a good result and in view of bone regrowth and interindividual variations. This dosing regime is based on experimental results. For non-smoking patients with peri-implantitis who had bone loss of more than 3 mm measured on intra-oral radiographs at the affected site, it was found that one year daily, oral administration of a silicon compound stopped the progressing bone loss and even improved the bone level at the affected implant site. In addition, the color of gums indicated an improved vascularization and an improved periodontal health status without inflammation.

In again a further embodiment, the silicon compound is used in a treatment after that a surgical operation has been carried out. The surgical operation is more particular the provision of a cut into the tissue surrounding a tooth or implant, needed for subsequent cleaning of the respective tooth or implant, such as with an antiseptic. Such surgical step is particularly necessary in case of deep pockets, which otherwise cannot be cleaned properly. The silicon compound is deemed to contribute to stimulation and regrowth of the bone and to healing of the tissue. In this application, the oral administration of the silicon compound together with a choline stabilizer is deemed highly advantageous, as the choline is deemed to have a positive impact on the tissue healing.

In again further embodiments, the silicon compound is used for the prevention of periodontitis and/or peri-implantitis. Particularly but not exclusively for preventive use, the administration of the bioavailable silicon compound is suitably combined with the administration of one or more vitamins and trace elements. Relevant vitamins and trace elements for both periodontitis and peri-implantitis comprise vitamin C, zinc, copper and selenium. Additional vitamins and trace elements include vitamin D, vitamin K, boron, calcium and magnesium. The administration of one or more of these additional vitamins and/or trace elements is deemed particularly relevant for peri-implantitis.

The silicon compound is administered for oral use. More particularly, the oral use is for absorption via the gastro-intestinal tract. Said absorption is also known as enteral use. It results is a systemic administration of the silicon compound, rather than a local, topical administration.

The silicon compound is preferably administered in an oral dosage form and with a dose in the range of 1-50 mg Si per day, preferably 3-20 mg Si per day, for instance 5-15 mg Si per day, such as 10 mg Si per day. When used in a preventive treatment, the dose is suitably lower than in a curative treatment. Suitably, the dosage of a preventive treatment is about 30-60% of that of a curative treatment. For instance, 3-6 mg Si per day is deemed effective for prevention, whereas 6-15 mg Si per day is preferred for treatment. Particularly in case of a curative treatment, it is deemed preferable to administer the silicon compound twice daily. It is surprising that such a small daily dosage turns out sufficient to have an effect on the tissue in the oral cavity. The dosage is particularly small when taking into account the oral administration. In fact, when the silicon compound is absorbed by the human body from the gastro-intestinal tract, and becomes available to the body.

More preferably, the silicon compound is administered daily during a period of at least three months in the case of periodontitis. Improvements were seen already after three months. Nevertheless, daily administration during a period of at least six months is considered beneficial in the case of periodontitis to maintain and enhance the achieved result and in view of interindividual variations of the human body.

Preferred patient groups are adult female and male patients. A first specific patient group is composed of patients with an increased bone turnover, which is known as a marker for risking osteoporosis. Another specific patient group are pregnant women. These patient groups are more susceptible to periodontitis, which need not be due to less hygiene, but to reduced silicon content in the body and/or a higher need thereof. Another specific patient group are smokers and or diabetic patients, who may have decreased vascularization of the gums.

The term 'bioavailable silicon compound' refers in the context to the invention to any silicon compound such that silicon (preferably in the form of silicic acid) is absorbed via the gastro-intestinal tract, into the blood circulation. The administration of silicon into the body is cumbersome, as absorption generally occurs as monosilicic acid, and this monomeric (and also dimeric, trimeric) silicic acid has an inherent tendency of polymerisation, which will result in silica that is no longer soluble in water and cannot be absorbed via the gastro-intestinal tract. The silicon compound in the composition for oral administration does not need to be monomeric, but is at least in such form that it may render silicic acid in a monomeric and/or oligomeric form in the gastro-intestinal tract. Preferably, for this use, the bioavailable silicon compound is stabilized with a stabilizing agent.

A preferred silicon compound for use in this treatment is a silicic acid. This is a form of silicon that is directly or indirectly bioavailable, in the sense of having the ability of absorption from the gastrointestinal tract into the blood. The bioavailable form of silicic acid is more particularly its monomer, orthosilicic acid. It is however not excluded that dimers, trimers and higher oligomers can also be absorbed. Furthermore, such higher oligomers may be condensated into lower oligomers (dimers, trimers etc) and monomers under the conditions residing in the stomach (low pH). The ultimate polymer that can be formed out of silicic acid is silica ($SiO_2$). Silica is however no longer bioavailable.

Another preferred group of silicon compounds are alkyl- and hydroxyl-substituted silanols, such as monomethyltrisilanol. Similarly to orthosilicic acid, these compounds may polymerize by intermolecular reactions between the silanol (Si—OH) groups.

In order to prevent polymerisation of the silicon compound, it is known to add a stabiliser. The stabiliser is deemed to act as a complexing agent of the silicon compound, and more particularly silicic acid. Typical stabilizers include amino acids, salicylic acid, sorbitol acid, ascorbic acid, lactic acid, caproic acid, peptides, carnitine, phenolic or polyphenolic compound such as vanillin (4-hydroxy-3-methoxybenzaldehyde), betaine and choline. The amino acids may be present in the form of protein hydrolysates, for instance of animal or vegetal origin. Such proteins are preferably fully hydrolysed to amino acids, though partial hydrolysis to something widely referred to as polypeptides and peptides, is not excluded. The applied stabilizer preferably contains at least one amino groups, including (charged) quaternary ammonium groups, in view thereof that a polar attraction may exist between the positive charge of the ammonium group and the dipolar oxygen atoms of the silicon compound, and more preferably silicic acid, which are rather negative. Also, the ammonium groups may fit well at a short distance of the substantially tetrahedrically arranged silanol groups of the silicic acid.

In a preferred embodiment of the invention, the silicon compound is stabilized or combined with choline or a choline derivative. Choline is a precursor of phospholipids which are essential components of cell membranes and is also involved in cell signalling (e.g. the neurotransmitter acetylcholine), lipid metabolism, the protection against homocysteine mediated breakdown of collagen fibers in bone and other connective tissue, and the suppression of inflammation and oxidative stress. It is believed that choline contributes to the positive outcome of the treatment of patients suffering from periodontitis and/or peri-implantitis.

The choline compound may be administered separately from the silicon compound or be integrated in the same composition as a stabilizer of the silicon compound. Preferably, the choline is integrated in the same composition. The choline compound may be chosen from group of choline, acetylcholine, betaine, glycerophosphorylcholine, sphingomyelin, phosphatidylcholine, lecithin and salts thereof. The preferred form is the use of choline and/or a salt thereof. A variety of choline salts is known, among which choline chloride, choline bitartate, choline hydroxide, choline dihydrogencitrate, choline 2-4-dichlorophenoxyacetate (2,4 D choline salt), choline acetate, choline carbonate, choline citrate, choline tartate, choline lactate, choline dibutyl phosphate; choline O,O'-diethyl dithiophosphate, choline dihydrogen phosphate; choline phosphate. Other choline salts are not excluded, as long as they meet requirements of pharmaceutically acceptable ingredients. Most preferably, the choline or its salt is used as a stabilising agent of the silicon compound. It is therein not excluded that further stabilizing agents for the silicon compound are used additionally.

In a further embodiment, the preparation further comprises a trace element. Examples thereof include magnesium, zinc, calcium, copper, boron and selenium. These elements, and particularly magnesium and/or calcium have a beneficial impact on bone formation, and are deemed very useful in the prevention and/or treatment of peri-implantitis. They can be incorporated in a preparation including silicic acid with a stabiliser such as choline. In again a further embodiment, the preparation further comprises a vitamin. Examples thereof are vitamin D, vitamin K and vitamin C. These vitamins promote connective tissue formation by stimulating bone metabolism and/or the biosynthesis of collagen. Rather than as part of the same preparation, vitamins and/or trace elements may further be administered separately from the preparation of the silicon compound. It is however deemed advantageous to include vitamins and/or trace elements into the same preparation, in order to enable compliance. As patients often are aware of the need of vitamin C consumption, it is most preferable to include vitamin D and vitamin K.

The preparation may be a liquid formulation or a solid formulation. As a solid formulation, use can be made of encapsulated pellets prepared by means of extrusion-spheronisation. Alternatively, use can be made of filled liquid capsules with a capsule shell comprising a hydroxyalkylcellulose or hydroxyalkylalkylcellulose, preferably hydroxypropylmethylcellulose as described in the non-prepublished application EP18164045 in the name of Applicant, which is herein included by reference. The capsule-in-capsule concept disclosed therein may be suitable to enable oral administration of a second medicament or nutrient in addition to the bioavailable silicon compound in a single dosage form. The second medicament or nutrient may moreover be chemically incompatible with the bioavailable silicon compound.

In another embodiment, the treatment involves the oral administration of a combination of a bioavailable silicon compound, preferably as silicic acid, optionally with at least one of the group comprising stabilizers, trace elements, and anti-inflammatory agents. Both in periodontitis and peri-implantitis inflammation of the gingiva occurs, resulting in red, swollen and tender gums. Anti-inflammatory agents will ameliorate these symptoms rapidly whereas the silicon compound will help regenerate the soft and hard periodontium structures.

In another embodiment, the treatment involves the oral administration of a combination of a bioavailable silicon compound, preferably as silicic acid, optionally with one or more of said stabilizers, trace elements and vitamins, and a probiotic strain and/or prebiotic composition. The use of viable probiotics strains are known to improve a balanced bacterial mouth flora which reduces periopathogenic bacteria to accumulate around teeth and implants, thereby preventing, at least partially, the cause behind periodontitis and/or peri-implantitis. Prebiotics are non-digestible fibers which stimulate the growth of beneficial bacteria. It is also believed that the use of probiotic strains and/or prebiotics contribute to a well balanced, healthy bacterial flora in the intestine which may increase the absorption of silicon.

In a further embodiment, the treatment involves the oral administration of a bioavailable silicon compound, preferably as silicic acid, optionally with one or more of said stabilizers, trace elements and vitamins, in combination with local use of antimicrobial agents, synthetic antiseptics and/or natural antiseptics. The local use is particularly administration in the mouth, for instance by means of a liquid preparation for washing or rinsing the mouth, or as an ingredient of a paste, microspheres, a gel, a chip, fibers or otherwise. The antimicrobial agent may alternatively or in addition be administrated systemically. Antibiotics are preferably applied either orally or locally inside the pocket. Duration of the treatment with an antibiotic is by further preference between 3 and 10 days, with for instance daily, twice daily, three times daily or four times daily application. Suitable antibiotics agents include penicillin, amoxicillin, augmentin, demeclocycline, doxycycline, minocycline, tetracycline, metronidazole or other nitroimidazoles, triamcinolone, clindamycine, azithromycin or other macrolides, moxifloxacin, ciprofloxacin or other quinolones, azithromycin or other lincomycin derivatives, any pharmaceutical acceptable salt thereof, and combinations thereof. The said antibiotic agent is for instance applied in a concentration up to 25 wt %. In a most preferred application, the antimicrobial agent is applied subgingival, for instance in the form of a gel, or encapsulated in bioavailable microspheres which are suspended in a gel carrier. The combination of respectively an oral bioavailable silicon compound, systemic antibiotics and a local antiseptic rinse is also possible.

The antiseptic agents are suitable for mouth disinfection and irrigation of the affected site. A suitable antiseptic agent is chlorhexidine and/or any of its pharmaceutically acceptable salts, such as chlorhexidine digluconate. As an adjunct to scaling and root planning, a chlorhexidine solution can be used for respectively rinsing the mouth, irrigating the periodontal pockets and cleaning the implants whereas a chlorhexidine gel is applied for brushing respectively the teeth and/or the implants and the tongue. The chlorhexidine solutions and gels are conventionally applied in a concentration of 0.5-1.5%, preferably 1 wt %, though lower concentrations, for instance 0.1-0.5 wt % are not excluded. Alternative antiseptic agents include sodium hypochlorite, povidone iodine and hydrogen peroxide. Surgical intervention may be needed to create an access flap, in order to facilitate the removal of subgingival bacterial and non-bacterial residues which stick to the lower parts of periodontium and/or the implants. Such surgical intervention, may be combined, in the case of advanced bone loss, with the local application of a bioactive substance which promotes bone growth such as de-proteinized bone mineral, bone grafts, or other bone substitutes with or without collagen membranes.

Simultaneous mouth disinfection by respectively irrigation of the pockets, cleaning and disinfecting the implants or teeth and/or the use of local and oral antimicrobial agents and/or the use of subgingival bioactive substances, together with oral administration of a bioavailable silicic acid has been found to lead to the best results.

BRIEF DESCRIPTION OF FIGURES

These and other aspects of the invention will be further elucidated with reference to the Examples and the Figures, wherein.

EXAMPLES

Example 1

A clinical test was carried out in a dental practice on periodontitis patients. 40 periodontitis patients were randomly selected. All 40 patients were given a standard treatment of scaling and root planning. The 40 patients were divided into two treatment groups of each 20 patients. The patients in the first treatment group were given a bioavailable form of silicon in solid form (bioavailable silicic acid) for oral administration twice a day. The biological form of silicon was commercially available under the trade name BioSil®, from Bio Minerals N.V., Destelbergen, Belgium. This formulation contains choline-stabilized orthosilicic acid (ch-OSA®), wherein silicic acid is stabilized with choline chloride. The formulation furthermore contains microcrystalline cellulose as a carrier. The solid, encapsulated formulation is prepared by extrusion and is packaged in magnetic induced sealed high density polyethylene bottles to ensure a constant humidity level. The remaining 20 patients were the control group. Patients were instructed to take two capsules per day, each capsule containing 5 mg Si, during six months. The treatment was evaluated by measuring respectively probing pocket depth (PPD), the percentage of teeth with PPD and bleeding on probing (BOP), before the start of the treatment (t=0) and after the treatment (t=6 months). Probing of pocket depth was performed with a calibrated probe (North Carolina periodontal probe, Hu-Friedy, Chicago, IL, USA).

Figure 1:
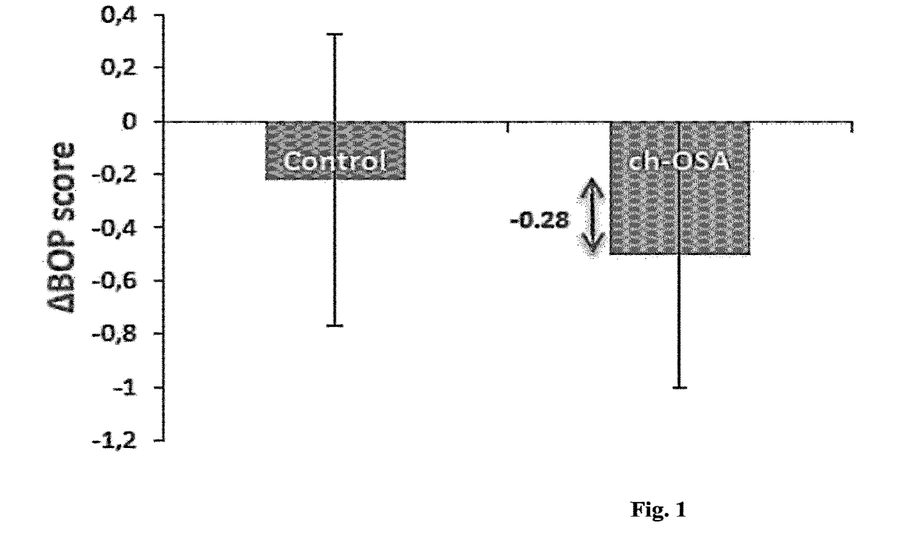
FIG. 1 shows change in BOP scores of periodontitis patients after 6 months standard treatment in combination with administration of oral bioavailable silicic acid in comparison to standard treatment only (control).

The results of the treatment on the probing pocket depth (PPD) are summarized in Table 1. These results demonstrate that the use of the silicon product as an add-on to the standard therapy resulted in a better improvement for deep pockets, i.e. pockets >4 mm, reaching statistical significance for pockets >5 mm (see table 1: change control versus change treatment). After six months oral silicon treatment the percentage of teeth with deep pockets decreased with 10% more compared to controls (change in treatment group: −70%, change in control group: −60%). The improvement in BOP over six months treatment was also greater when the standard therapy was combined with the administration of bioavailable silicic acid, as shown in FIG. 1.

|  |  | Treatment group | | | |
| --- | --- | --- | --- | --- | --- |
|  |  | Control (n = 20) | | Treatment with bioavailable silicic acid | |
| Variable | Time (months) | Mean* | Change* | Mean* | Change* |
| Overall | 0 | 4.47 ± 0.83 |  | 4.89 ± 1.04 |  |
| Overall | 6 | 2.67 ± 0.34 | −1.80 ± 0.81 | 2.75 ± 0.37 | −2.14 ± 0.92 |
| Undeep pockets (<4 mm) | 0 | 3.39 ± 0.36 |  | 3.40 ± 0.26 |  |
| Undeep pockets (<4 mm) | 6 | 2.39 ± 0.27 | −1.00 ± 0.47 | 2.46 ± 0.36 | −0.94 ± 0.45 |
| Deep pockets (4 ≤ P ≤ 7 mm) | 0 | 5.00 ± 0.46 |  | 5.17 ± 0.63 |  |
| Deep pockets (4 ≤ P ≤ 7 mm) | 6 | 2.89 ± 0.43 | −2.10 ± 0.63 | 2.80 ± 0.33 | −2.38 ± 0.65 |
| Deeper pockets (≥5 mm) | 0 | 5.57 ± 0.41 |  | 5.69 ± 0.51 |  |
| Deeper pockets (≥5 mm) | 6 | 3.24 ± 0.63 | −2.33 ± 0.70 | 2.93 ± 0.39 | −2.76 ± 0.59** |
| Very deep pockets (≥6 mm) | 0 | 6.27 ± 0.21 |  | 6.42 ± 0.26 |  |
| Very deep pockets (≥6 mm) | 6 | 3.34 ± 0.69 | −2.94 ± 0.67 | 3.26 ± 0.63 | −3.16 ± 0.59 |
| Deepest pockets (≥7 mm) | 0 | 7.17 ± 0.24 |  | 7.14 ± 0.19 |  |
| Deepest pockets (≥7 mm) | 6 | 4.01 ± 0.26 | −3.16 ± 0.02 | 3.55 ± 0.95 | −3.59 ± 1.03 |

Probing Pocket depth (PPD) in mm; *including standard deviation, **$p < 0.05$ versus control.

Example 2

A clinical test was carried out in a dental practice on periodontitis patients with residual pockets. 10 periodontitis patients were randomly selected who received the standard treatment (scaling and root planning) but remain to have deep pockets despite of the standard treatment.

Following the standard treatment, all 10 patients were administered orally a bioavailable form of silicon in solid form, as commercially available under the trade name Bio-Sil®, from Bio Minerals N.V., Destelbergen, Belgium. This formulation contains choline-stabilized orthosilicic acid (ch-OSA®), wherein silicic acid is stabilized with choline chloride. The formulation furthermore contains microcrystalline cellulose as a carrier. The solid, encapsulated formulation is prepared by extrusion and is packaged in magnetic induced sealed high density polyethylene bottles to ensure a constant humidity level. The treatment was evaluated by measuring respectively probing pocket depth (PPD) and bleeding on probing (BOP), before the start of the treatment (t=0) and after the treatment (t=6 months). Probing of pocket depth was performed with a calibrated probe (North Carolina periodontal probe, Hu-Friedy, Chicago, IL, USA).

Figure 2A:
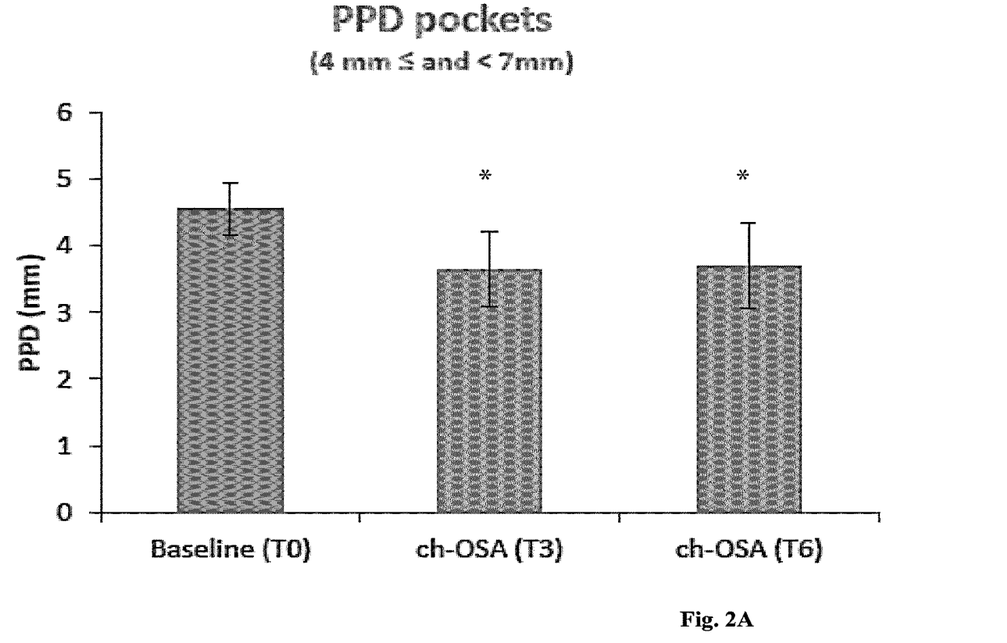
FIG. 2A and FIG. 2B show PPD scores (FIG. 2a) and BOP scores (FIG. 2b) of periodontitis patients (n=10) with residual pockets (following standard treatment) prior to oral administration of bioavailable silicic acid (baseline) and after 3 and 6 months of administration of bioavailable silicic acid; *p<0.05 versus baseline.
Figure 2B:
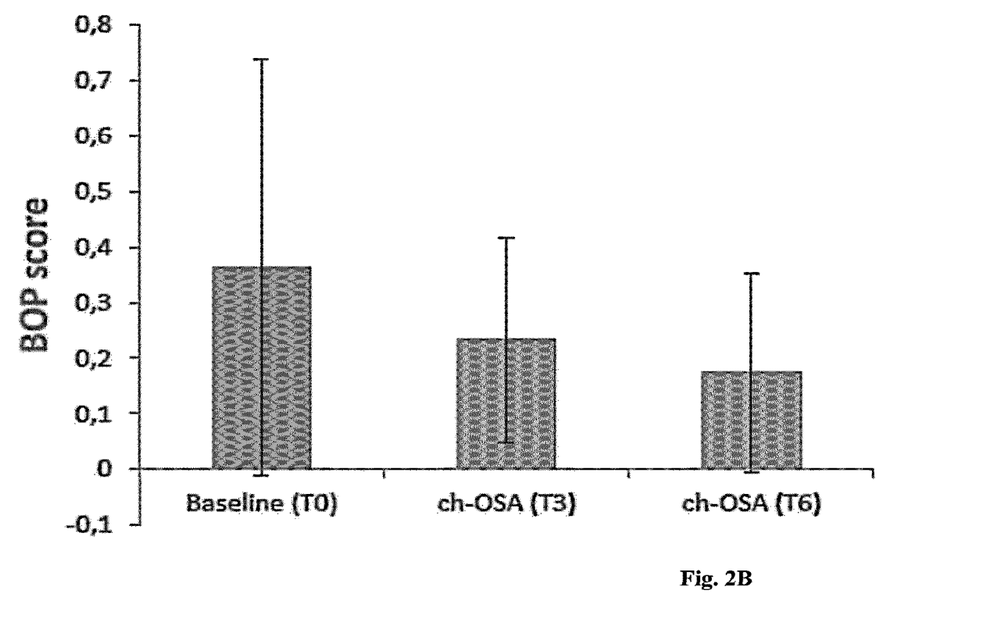

The results are visualized in FIGS. 2a and 2b. As a result of only the oral ch-OSA supplementation, both the PPD and the BOP decreased already after 3 months. An additional benefit was seen for BOP after 6 months treatment. PPD was statistical significantly lower after 3 and 6 months oral ch-OSA supplementation versus baseline.

Example 3

Figure 3A:
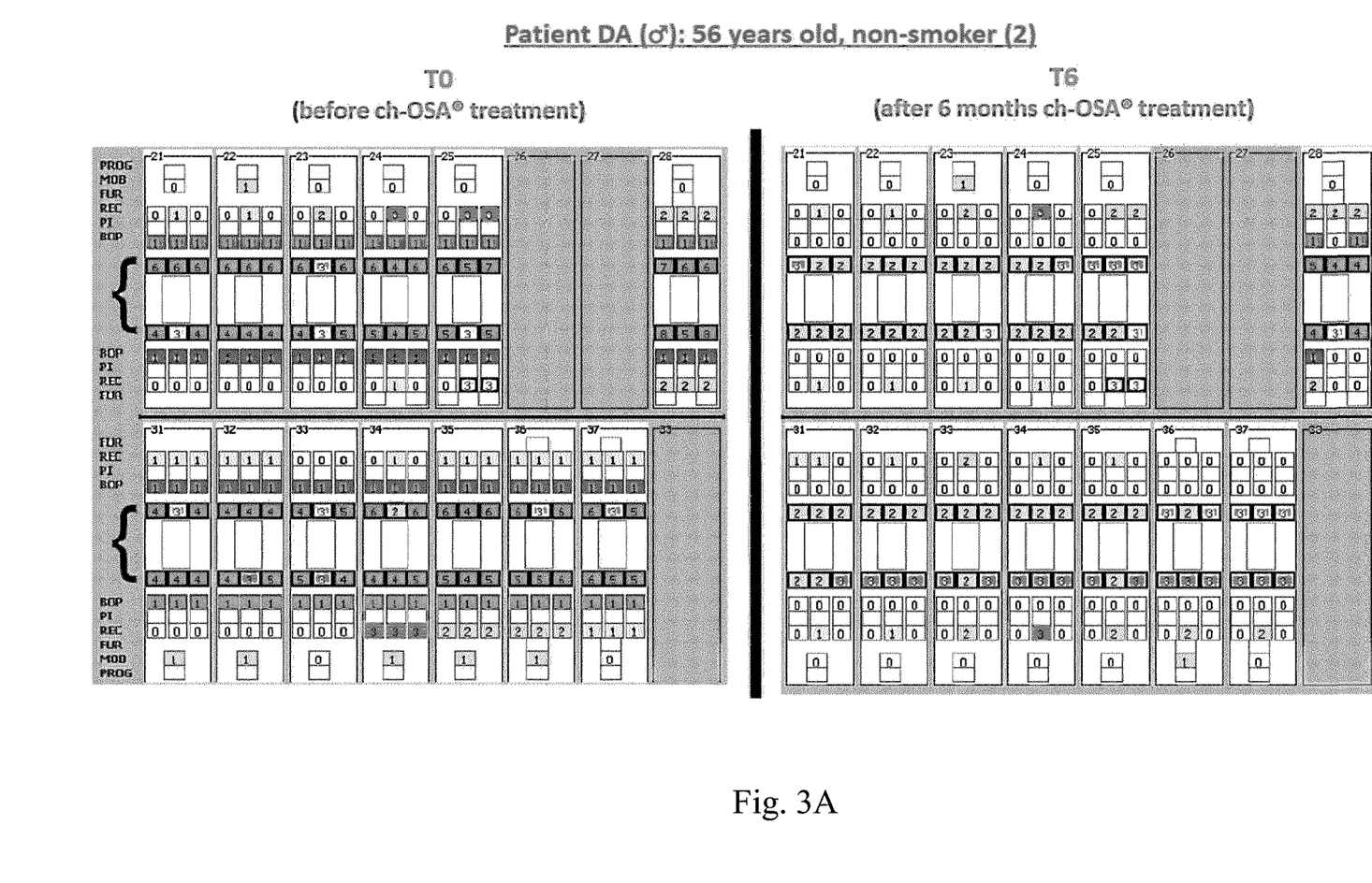
FIGS. 3A and 3B show schematically the scale of periodontitis for two individual patients. The situation is shown in the form of a map of dents, both in the baseline, and after a treatment during three and six months by oral administration of bioavailable silicic acid.
Figure 3B:
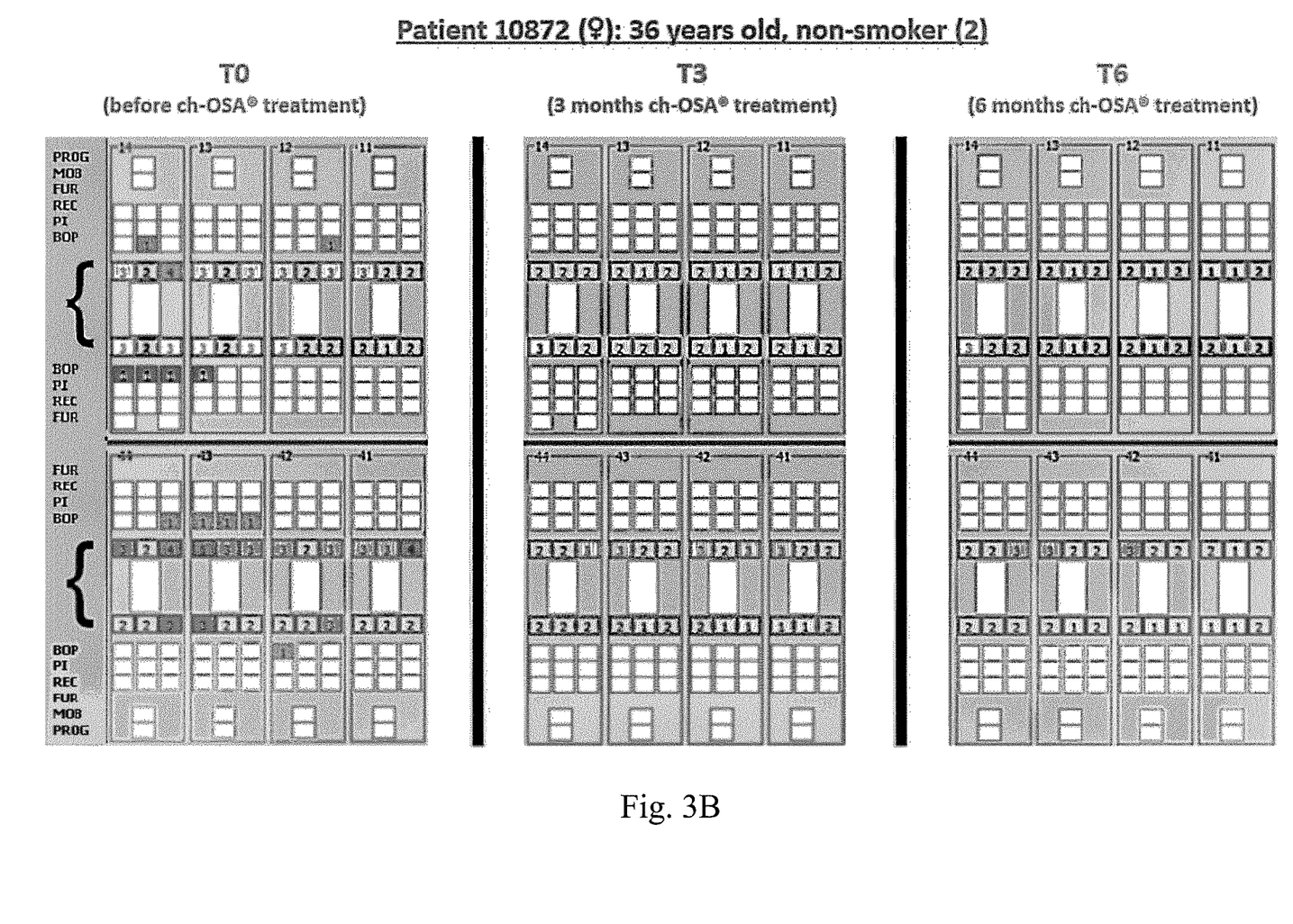

Two individual patients with chronic periodontitis were administrated bioavailable silicic acid in the form of choline-stabilized orthosilicic acid (ch-OSA®), wherein silicic acid is stabilized with choline chloride. The first patient was a non-smoking male patient of 56 years old. The second patient was a non-smoking female patient of 36 years old. The results are shown in FIGS. 3A and 3B, wherein the color provides an indication of the pocket depth. The actual depth is also indicated for each tooth. The data were obtained by measuring the pocket depth around each tooth in the mouth 6 times. In both cases, the periodontitis reduced significantly. Before the treatment, patients had very deep pockets. After the treatment, this was reduced to low depth (less than 3 mm).

Example 4

Figure 4A:
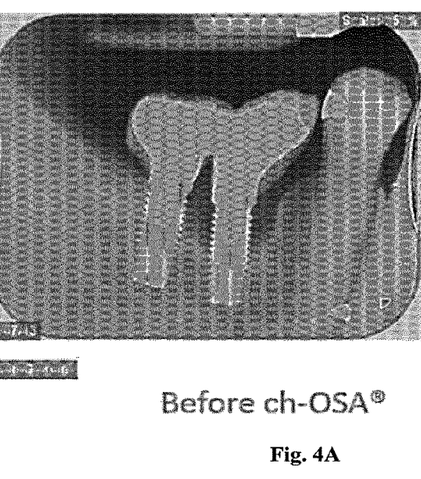
FIGS. 4A and 4B are X-ray photographs of an implant of a female patient having peri-implantitis, before and after a one year treatment by oral administration of bioavailable silicic acid.
Figure 4B:
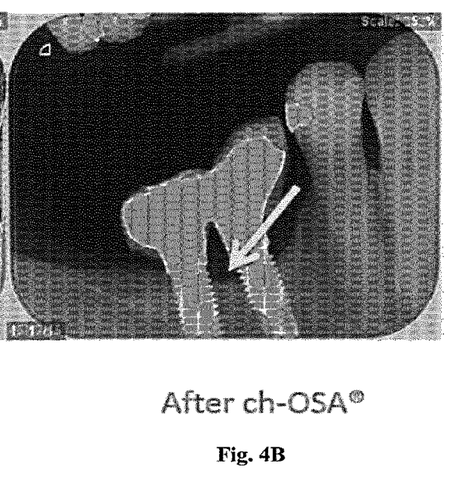

A female peri-implantitis patient, 66 years old and non-smoker, had severe bone loss at two implant sites (as shown in FIG. 4A). The patient took during one year 5 drops of BioSil® liquid twice daily. This formulation contains choline-stabilized orthosilicic acid (ch-OSA®), wherein silicic acid is stabilized with choline chloride. The formulation furthermore contains glycerol as a diluent. After one year the bone level was significantly increased at the implant site (see FIG. 4B).

Figure 5A:
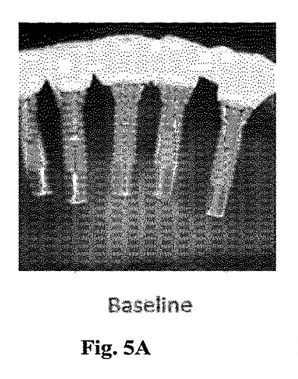
FIG. 5A-5C are X-ray photographs of an implant of a female patient having peri-implantitis with severe bone loss (A) and damaged gingiva, as baseline, after 6 months and after 12 months treatment by oral administration of bioavailable silicic acid
Figure 5B:
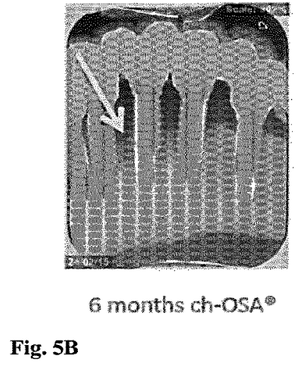
Figure 5C:
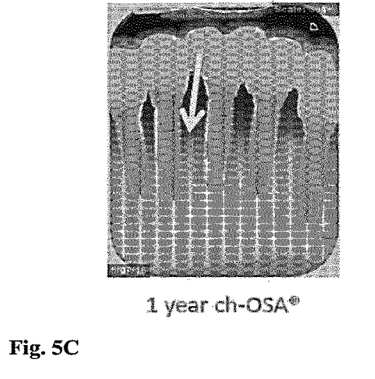
Figure 6:
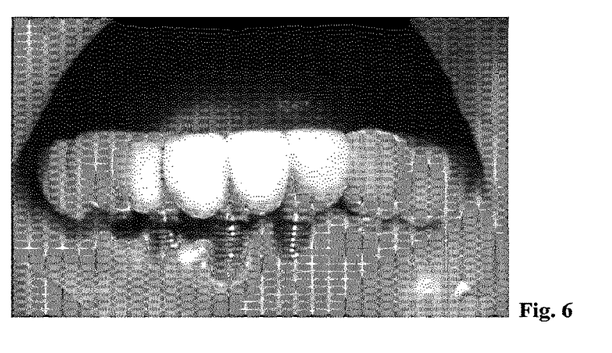
FIG. 6 is a photograph of a mouth of a patient with an implantate showing the state after the treatment with the compound of the invention.

A second peri-implantitis patient, 73 years and non-smoker, with severe bone loss at the implant sites and damaged gingiva (FIG. 5a) took during one year 5 drops of BioSil® liquid twice daily. After one year the bone level was also significantly increased at the implant site (FIG. 5b, after 6 months, FIG. 5c, after 12 months). FIG. 6 shows that the gingiva regained its normal appearance with good color indicating improved vascularization in the course of the 1 year treatment.

The following treatment examples can be used as an adjunct to good mouth hygiene, scaling and root planing:

Example 5: Combination Treatment for the Prevention of Periodontitis

Daily oral administration of 5 mg of bioavailable silicic acid in the form of choline-stabilized orthosilicic acid (ch-OSA®), wherein silicic acid is stabilized with choline chloride, for instance in the form of a capsule.

Daily administration of a tablet containing 200 mg vitamin C, 150 microgram selenium, 10 mg zinc, 1 mg copper.

Example 6: Combination Treatment for the Prevention of Peri-Implantitis

Daily oral administration of 5 mg of bioavailable silicic acid in the form of choline-stabilized orthosilicic acid (ch-OSA®), wherein silicic acid is stabilized with choline chloride, for instance in the form of a capsule;

Daily administration of 1000 mg calcium, 6 microgram vitamin D, 50 microgram vitamin K, preferably in two formulations, such as tablets;

Daily administration of 200 mg vitamin C, 100 microgram selenium, 10 mg zinc, 1 mg copper, 0.5 mg boron, 200 mg magnesium, for instance in the form of a single formulation, such as a tablet.

Example 6: Combination for Use in the Treatment of Periodontitis 6 months oral administration of 10 mg of a bioavailable silicon compound per day, which bioavailable silicon compound is in the form of choline-stabilized orthosilicic acid (ch-OSA®), wherein silicic acid is stabilized with choline chloride; 10 mg bioavailable silicon is preferably administered as two dosage units, each containing 5 mg bioavailable silicon, for instance as a tablet;
mouth rinsing with chlorhexidine 1% solution twice daily during 4 weeks.

It is herein preferable, that the administration of the bioavailable silicic acid and the mouth rinsing start simultaneously.

Example 7: Combination for Use in the Treatment of Periodontitis

Initial full mouth one-stage disinfection by rinsing for 2 minutes with a 0.12% chlorhexidine solution.
6 months oral administration of 10 mg of bioavailable silicic acid in the form of choline-stabilized orthosilicic acid (ch-OSA®), wherein silicic acid is stabilized with choline chloride, suitably in the form of two dosage units each containing 5 mg bioavailable silicic acid;
Daily administration of two probiotic lozenges, each containing 2 viable strains of *Lactobacillus reuteri* (1 $10^8$ CFU), for instance DSM17938 and ATCC PTA5289, during 6 months.

It is herein preferable, that the administration of the bioavailable silicic acid and the administration of the probiotic lozenges start simultaneously. Alternatively, the administration of the bioavailable silicic acid may precede the administration of the probiotic lozenges during a preparatory period of for instance 3 days up to 14 days, for instance 1 week.

Example 8: Combination for Use in the Treatment of Aggressive Periodontitis 6 months oral administration of 10 mg of bioavailable silicic acid per day, in the form of choline-stabilized orthosilicic acid (ch-OSA®), wherein silicic acid is stabilized with choline chloride;
Oral administration of amoxicillin (250 mg three times daily) with metronidazole (250 mg three times daily) during 1 week, and
mouth rinsing with chlorhexidine 1% solution twice daily during 4 weeks.

Example 9: Aggressive Periodontitis Treatment 6 months oral administration of 10 mg of bioavailable silicic acid per day, in the form of choline-stabilized orthosilicic acid (ch-OSA®), wherein silicic acid is stabilized with choline chloride, for instance in the form of 2 dosage units
combined oral administration of amoxicillin (250 mg three times daily) with metronidazole (250 mg three times daily) during 1 week and Subgingival placement of 2.5 mg chlorhexidine gluconate in a hydrolyzed gelatin matrix chip (PerioChip). The chip degrades within 7-10 days.

It is herein preferable, that the administration of the bioavailable silicic acid and the administration of the antibiotic start simultaneously and concur with the subgingival placement. However, alternative protocols are not excluded.

Example 10: Aggressive Periodontitis Treatment 6 months oral administration of 10 mg of bioavailable silicic acid per day in the form of choline-stabilized orthosilicic acid (ch-OSA®), wherein silicic acid is stabilized with choline chloride; preferably in the form of two dosage units, such as tablets
Local application of an ethylene/vinyl acetate copolymer fiber that contains tetracycline (12.7 mg per 9 inches) in the affected periodontal pocket for 10 days.
mouth rinsing with chlorhexidine 1% solution twice daily during 4 weeks.

Example 11: Combination in the Treatment of Peri-Implantitis 12 months oral administration of 10 mg of bioavailable silicic acid per day in the form of choline-stabilized orthosilicic acid (ch-OSA®), wherein silicic acid is stabilized with choline chloride, preferably in the form of two dosage units, such as capsules.
Daily administration of 1000 mg calcium, 6 microgram vitamin D, 50 microgram vitamin K, preferably in the form of two dosage units, such as tablets.
Daily administration of 200 mg vitamin C, 100 microgram selenium, 10 mg zinc, 1 mg copper, 0.5 mg boron, 200 mg magnesium, preferably in the form of a table.
irrigating the periodontal pockets and cleaning the implants with chlorhexidine 1% solution
mouth rinsing with chlorhexidine 1% solution twice daily during 4 weeks.

Example 12: Combination for Use in the Treatment of Peri-Implantitis 12 months oral administration of 10 mg of bioavailable silicic acid per day in the form of choline-stabilized orthosilicic acid (ch-OSA®), wherein silicic acid is stabilized with choline chloride, for instance in the form of two dosage units such as capsules.
Surgical intervention to create an access flap, removal of subgingival bacterial and non-bacterial residues, irrigation of the periodontal pockets and cleaning the implants with chlorhexidine 1% solution. Use of deproteinized bone mineral on a collagen membrane.
Mouth rinsing with chlorhexidine 1% solution twice daily during 4 weeks.
Daily administration of 1000 mg calcium, 6 microgram vitamin D, 50 microgram vitamin K, for instance in the form of two dosage units, such as tablets.
Daily administration of 200 mg vitamin C, 100 microgram selenium, 10 mg zinc, 1 mg copper, 0.5 mg boron, 200 mg magnesium, for instance in the form of a tablet.

In any of the above examples where the use of an antiseptic and/or antibiotics is combined with the oral administration of a bioavailable silicon compound, it is preferred that the administration of the silicon compound starts simultaneous with the use of the antiseptic and/or antibiotics. However, alternatively, the administration of the bioavailable silicic acid may precede the administration of the antiseptic and/or antibiotics during a preparatory period of for instance 3 days up to 14 days, for instance 1 week.

In summary, these examples indicate that the oral administration of a bioavailable silicon compound, such as silicic acid during a period of at least 3 months daily leads to inhibition of periodontitis and peri-implantatis and is thus a therapeutic effective, non-invasive, non-surgical treatment. The treatment is particularly suitable in combination with appropriate cleaning of the mouth, by one or more antiseptic and/or antimicrobial agent(s), in case the plaques are subgingival and difficult to reach a surgical created access flap may be needed. The treatment may be further enhanced by simultaneous administration of vitamins, such as vitamin C, Vitamin D, vitamin K, and/or trace elements, such as magnesium, calcium, selenium, boron and copper, as well as by administration of a probioticum or the use of subgingival bioactive substances. The positive results for chronic periodontitis indicate the major benefit of the present invention. The positive results for peri-implantitis provide a non-invasive treatment for this disease. Both positive results are by themselves highly surprising, in view thereof that a daily dose of bioavailable silicic acid may inhibit and even heal the disease that is already in an advanced state. The invention further relates to a method of prevention, inhibition or treatment of periodontitis and/or peri-implantitis comprising the oral administration of a bioavailable silicic acid.

The invention claimed is:

1. A method for inhibition and/or treatment of periodontitis and/or peri-implantitis in a patient, the method comprising enteral administering by mouth to a patient a bioavailable silicon composition, the bioavailable silicon composition comprising a bioavailable silicon compound according to formula (I) or an oligomer thereof $$Y_xSi(OH)_{4-x} \qquad (I)$$

wherein:
Y is optionally substituted $(C_1-C_4)$-alkyl, $(C_2-C_5)$-alkenyl, $(C_1-C_4)$-alkoxy, amino and
x is 0-2.

2. The method as claimed in claim 1, wherein the bioavailable silicon compound is a silicic acid (x=0).

3. The method as claimed in claim 1, wherein the bioavailable silicon compound is stabilized with a stabilizing agent.

4. The method as claimed in claim 3, wherein the bioavailable silicon compound is administered together with a choline compound as the stabilizing agent, and the choline compound is selected from the group consisting of choline, choline hydroxide, acetylcholine, betaine, glycerophosphorylcholine, phosphatidylcholine or a salt thereof.

5. The method as claimed in claim 1, wherein the bioavailable silicon composition is administered in the form of a capsule, tablet, liquid or granules.

6. The method as claimed in claim 1, wherein the bioavailable silicon compound is absorbed via the gastrointestinal tract.

7. The method as claimed in claim 1, wherein the bioavailable silicon compound is administered in an amount of 1-50 mg Si per day, 5-20 mg Si per day, 8-15 mg Si per day, or 10 mg Si per day.

8. The method as claimed in claim 7, wherein the bioavailable silicon compound is administered daily during a period of at least three months, during a period of at least six months or during a period of at least one year.

9. The method as claimed in claim 1, wherein the bioavailable silicon compound reduces bleeding of probing (BOP), and/or probing pocket depth (PPD).

10. The method as claimed in claim 9, wherein the bioavailable silicon compound reduces probing pocket depth (PPD) in patients having a PPD value of at least 4 mm in one or more teeth.

11. The method as claimed in claim 1, wherein the method is for inhibition and/or treatment of peri-implantitis.

12. The method as claimed in claim 1, wherein the method is for inhibition and/or treatment of periodontitis.

13. The method as claimed in claim 2, wherein the silicic acid is orthosilicic acid and/or its oligomers.

14. The method as claimed in claim 4, wherein the choline compound salt is selected from the group consisting of choline chloride, choline bitartate, choline dihydrogencitrate, choline 2-4-dichlorophenoxyacetate (2,4 D choline salt), choline acetate, choline carbonate, choline citrate, choline tartate, choline lactate, choline dibutyl phosphate; choline O,O'-diethyl dithiophosphate, choline dihydrogen phosphate; and choline phosphate.

15. The method as claimed in claim 1, further comprising administering a trace element and/or a vitamin selected from the group consisting of Vitamin C, Vitamin D and Vitamin K.

16. The method as claimed in claim 15, wherein the trace element is selected from the group consisting of magnesium, zinc, calcium, copper, boron and selenium.

17. The method as claimed in claim 1, further comprising administering an antiseptic agent, an antimicrobial agent, a probioticum, prebiotics, and/or a trace element and/or a vitamin chosen from the group of Vitamin C, Vitamin D and Vitamin K.

18. The method as claimed in claim 17, wherein the trace element is selected from the group consisting of magnesium, zinc, calcium, copper, boron and selenium.

19. The method as claimed in claim 1, further comprising administering a probioticum.

* * * * *